United States Patent
Lam et al.

(10) Patent No.: US 7,335,163 B2
(45) Date of Patent: *Feb. 26, 2008

(54) COMBINED COMPUTER MOUSE AND BLOOD PRESSURE SPHYGMOMANOMETER

(75) Inventors: Phillip L. Lam, Monterey Park, CA (US); Ping Cheng Benjamin Liu, San Gabriel, CA (US)

(73) Assignee: CalHealth, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/799,443

(22) Filed: Apr. 30, 2007

(65) Prior Publication Data
US 2007/0232937 A1    Oct. 4, 2007

Related U.S. Application Data

(62) Division of application No. 11/215,983, filed on Aug. 31, 2005, now Pat. No. 7,066,890.

(60) Provisional application No. 60/857,100, filed on Nov. 6, 2006.

(51) Int. Cl.
*A61B 5/00* (2006.01)
(52) U.S. Cl. .................. 600/490; 600/499; 600/500
(58) Field of Classification Search ............ None
See application file for complete search history.

(56) References Cited

U.S. PATENT DOCUMENTS 6,616,613 B1 *  9/2003  Goodman ............... 600/504
7,066,890 B1 *  6/2006  Lam et al. ............... 600/485
2006/0007151 A1 *  1/2006  Ram ........................ 345/163

* cited by examiner

Primary Examiner—Charles A. Marmor, II
(74) Attorney, Agent, or Firm—Leonard Tachner (57) ABSTRACT

A sphygmomanometer cuff assembly, air pump, pressure sensor and release valve are contained in an otherwise conventional computer mouse controller. Various alternative embodiments are illustrated and discussed herein. In one such embodiment the sphygmomanometer cuff is nominally positioned within the mouse structure and is extended outside the mouse housing during the measurement. In another embodiment, the cuff is always external of the mouse structure and is easily connected to the mouse at special ports during the measurement. In yet another embodiment, the cuff is always internal of the mouse structure and is readily accessible through an aperture in the housing surface of the mouse to permit the measurement to take place. Preferably, in each of these alternative embodiments a hinged or slidable door or panel protects the cuff or cuff ports between measurements. In some of the embodiments shown herein, the sphygmomanometer cuff is configured for receiving a human finger in circumambient pressured engagement using controlled air pressure to vary the cuff/finger engagement pressure in a precise manner. In one embodiment hereof, the sphygmomanometer cuff is configured as a wrist cuff.

2 Claims, 16 Drawing Sheets

COMBINED COMPUTER MOUSE AND BLOOD PRESSURE SPHYGMOMANOMETER

CROSS-REFERENCE TO RELATED APPLICATIONS

This application takes priority from U.S. Provisional Patent Application Ser. No. 60/857,100 filed Nov. 6, 2006 which takes priority from pending U.S. patent application Ser. No. 11/418,639 filed on May 5, 2006, which is a divisional of U.S. patent application Ser. No. 11/215,983 filed Aug. 31, 2005 and now issued U.S. Pat. No. 7,066,890.

BACKGROUND OF THE INVENTION

1. Field of the Invention

The present invention relates generally to blood pressure monitoring devices. More specifically, the invention hereof relates to a computer mouse controller which incorporates a blood pressure finger or wrist cuff for monitoring blood pressure and transmitting measured data to the computer with which the mouse is associated. Such data is then displayed on the display of the computer to provide an easily understood representation of the measured parameters.

2. Background Art

Hypertension is one of modern society's most insidious diseases. Left untreated, it causes life-threatening problems including atherosclerosis, strokes and aneurysms. Long-term hypertension can result in diminished cardio-vascular and kidney function. Yet while high blood pressure is one of the simplest problems to detect in an entirely non-invasive process, it is all too commonly undetected in a large portion of the population. In the past twenty years or so, with the advent of low-cost microprocessor chips and miniature digital electronics and electromagnetic devices, the self-measurement of blood pressure by non-medical personnel has become more readily available. Nevertheless, blood pressure sphygmomanometers are still too sophisticated for a large segment of the population. Even those who are entirely capable of operating such devices tend to put them away in drawers and other out of the way places where they often remain mostly forgotten and unused.

It would be highly advantageous to the early detection of hypertension and thus to the general health of the population if there were a way to provide prolific availability of blood pressure monitoring devices that were readily accessible and even easier to use than currently available digital sphygmomanometers. Having a blood pressure sphygmomanometer at virtually every computer with a pressure cuff always immediately adjacent to each such computer, would go a long way to serving such an advantageous function. Such is the purpose of the present invention.

SUMMARY OF THE INVENTION

The present invention combines the blood pressure sphygmomanometer with one of the most commonly available devices of the modern world, the computer mouse. Moreover, the invention incorporates the sphygmomanometer cuff into the computer mouse in a manner which makes it extremely simple and convenient to initiate and carry out the blood pressure measurement process. Three alternative embodiments are illustrated and discussed herein. In one such embodiment the sphygmomanometer cuff is nominally positioned within the mouse structure and is extended outside the mouse housing during the measurement. In another embodiment, the cuff is always external of the mouse structure and is easily connected to the mouse at special ports during the measurement. In yet another embodiment, the cuff is always internal of the mouse structure and is readily accessible through an aperture in the housing surface of the mouse to permit the measurement to take place. Preferably, in each of these alternative embodiments a hinged or slidable door or panel protects the cuff or cuff ports between measurements. In some of the embodiments shown herein, the sphygmomanometer cuff is configured for receiving a human finger in circumambient pressured engagement using controlled air pressure to vary the cuff/finger engagement pressure in a precise manner. In one embodiment hereof, the cuff is designed to engage the wrist.

In a well-known manner used in blood pressure sphygmomanometers of all kinds, the pressure of the cuff/finger engagement is initially increased until arterial vessel pulsation is beyond cutoff (total occlusion of the artery). The cuff pressure is then slowly decreased until first detection of arterial vessel pulsation (commonly known as Korotkoff Phase I). The corresponding cuff pressure at this point will be substantially equal to systolic blood pressure which is one significant parameter to be monitored. As cuff pressure continues to be decreased, arterial vessel pulsations will eventually become undetectable through the cuff because of the lack of adequate cuff pressure to sense those pulsations (commonly known as Korotkoff Phase V). The pressure of the cuff at this point will be substantially equal to diastolic blood pressure which is another significant parameter to be monitored. Moreover, the frequency of pulsations sensed between the systolic and diastolic pressures is measured and will be substantially equal to the heartbeat rate or pulse rate which is also a parameter of some significance to be monitored. These two cuff pressures and the pulsation frequency are the measured parameter data of the process and corresponding digital data are sent to the computer to which the mouse controller is associated.

Computer software, to be described herein, can then utilize this digital data (typically in binary form) to create a suitable display of the measured parameters on the computer's monitor. Other functions can also be carried out such as recording the data, graphically plotting data over numerous measurements and communicating the data to others such as by means of the internet for example by e-mail to pre-assigned medical personnel.

The principal advantage of the present invention is therefore clearly the proliferation of a simple and convenient way for the great number of computer users to have the benefits of frequent blood pressure monitoring. Moreover, because the computer mouse can normally be readily replaced in existing computers, this clearly beneficial health-related device can be enjoyed by substantially every computer user and his or her family with relatively little investment. Additionally, society as a whole will benefit from the likely increase in the early detection of hypertension and the resulting timely treatment thereof and prevention of related diseases. Thus it is believed that the present invention has the potential of leading to a profound change in both the configuration of computer mouse controllers and in the number of early detected hypertensive individuals.

BRIEF DESCRIPTION OF THE DRAWINGS

The various embodiments, features and advances of the present invention will be understood more completely hereinafter as a result of a detailed description thereof in which reference will be made to the following drawings.

DETAILED DESCRIPTION OF PREFERRED EMBODIMENTS

Referring to the accompanying figures and to FIGS. 1 through 6 initially, it will be seen that a first embodiment mouse controller 10 comprises a housing 12, click buttons 13 and 15 and control device 14. It will be understood that the precise configuration of the mouse controller hereof may be varied to virtually any of the many conventional designs. Therefore the shape, location and number of click buttons, the control device 14 and the shape of the housing 12 are all shown herein as illustrative only and should not be deemed limiting of the scope hereof. However, what is a significant improvement over conventional mouse controllers now follows.

Figure 1:
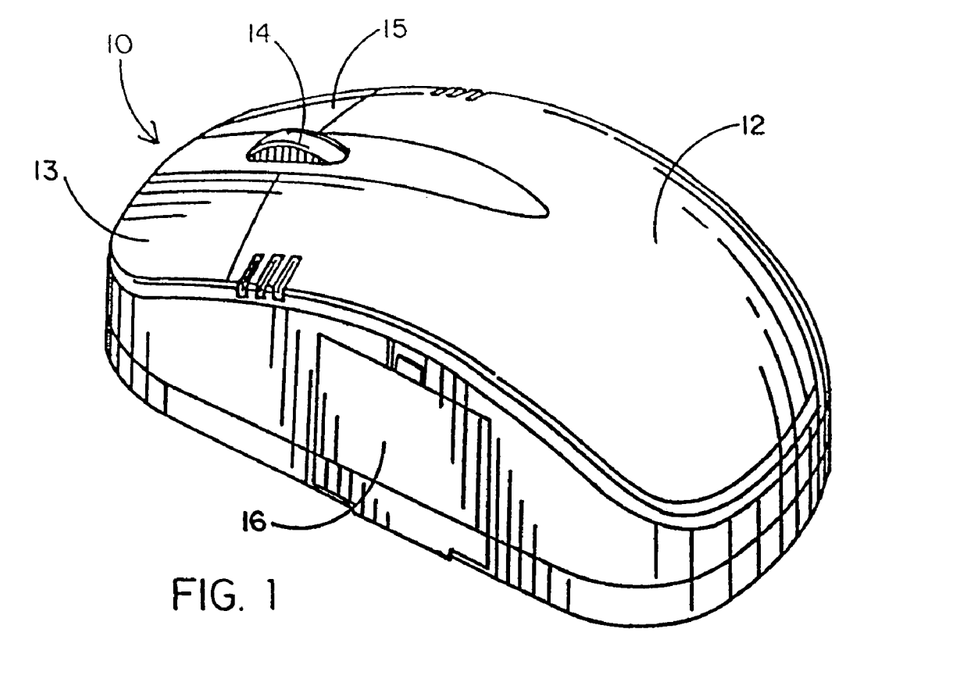
FIGS. 1 through 6 are various views of a first embodiment of the invention in which a sphygmomanometer pressure cuff is selectively ejected from within a mouse controller for blood pressure measurement.
Figure 2:
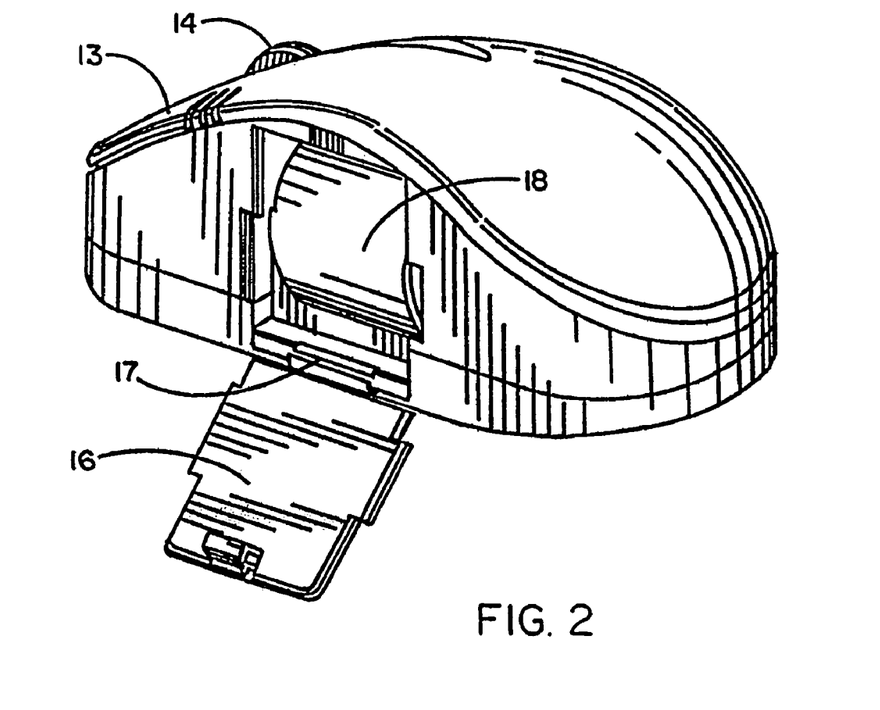
Figure 3:
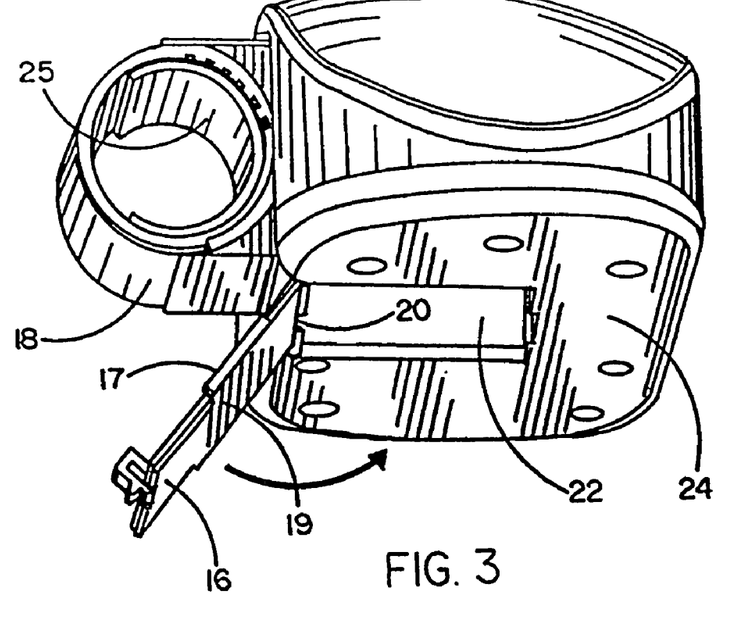
Figure 4:
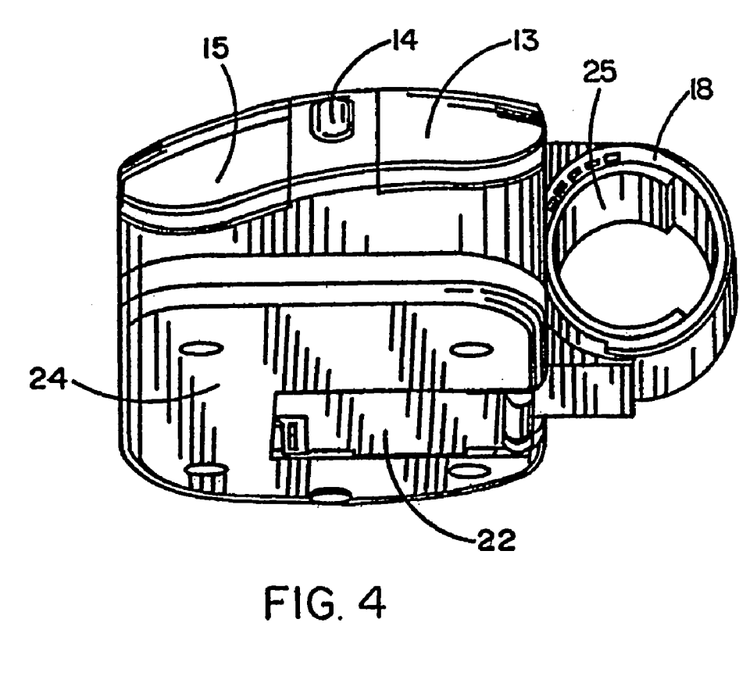
Figure 5:
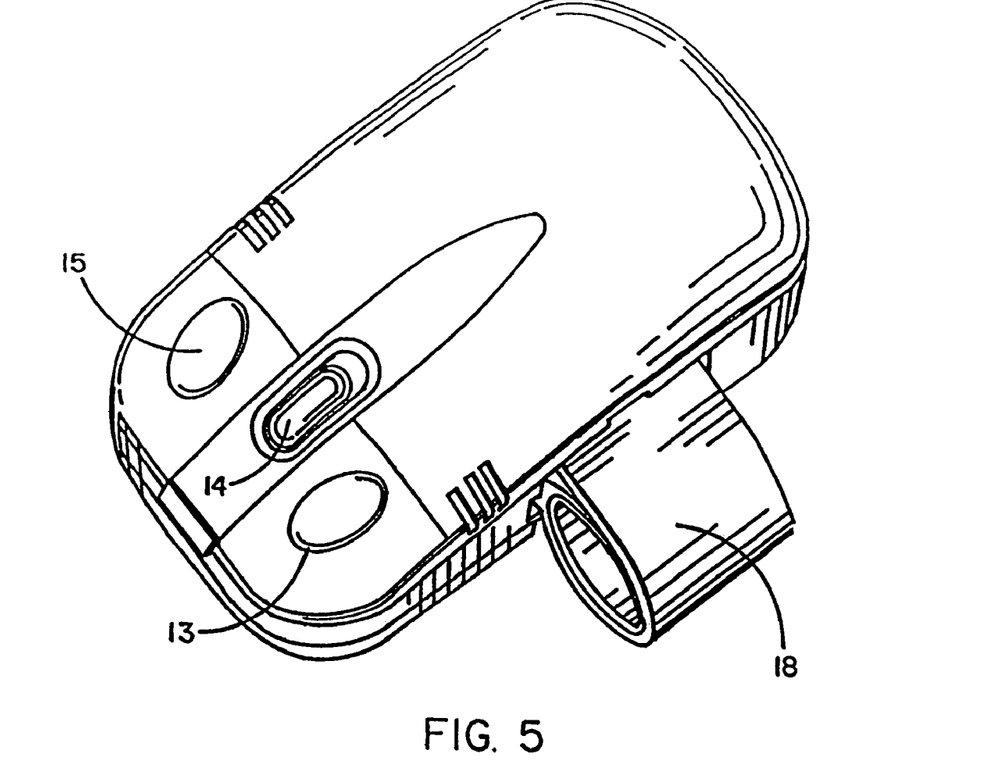

As seen in FIGS. 1 and 2, a hinged door 16 is provided on the side of mouse housing 12. Hinged door 16, when opened about a hinge 17, leads to the interior of housing 12 where a sphygmomanometer 21 and its cuff assembly 18 are located. As will be hereafter more fully described, upon activation of the sphygmomanometer 21, cuff assembly 18 extends through door 16 to the exterior of the mouse housing as shown best in FIGS. 3 to 5. This extension of the cuff assembly is facilitated by folding door 16 about hinge 17 until it is in alignment with an inner door stage 19 which is, in turn, extended beyond the housing 12 and rotated about its hinge 20 until the door assembly is fully rotated about 270 degrees into a rectangular recess 22 in the bottom surface 24 of the housing as shown in FIGS. 3 and 4 in particular. When the cuff assembly 18 is fully extended into the position shown in FIG. 5, the cuff assembly is in suitable position for insertion of a person's extended finger for measurement of blood pressure and pulse rate. The assembly may then be re-inserted into the housing and the door assembly rotated back into position for closure of the housing and normal, conventional usage of the mouse controller 10.

Figure 6:
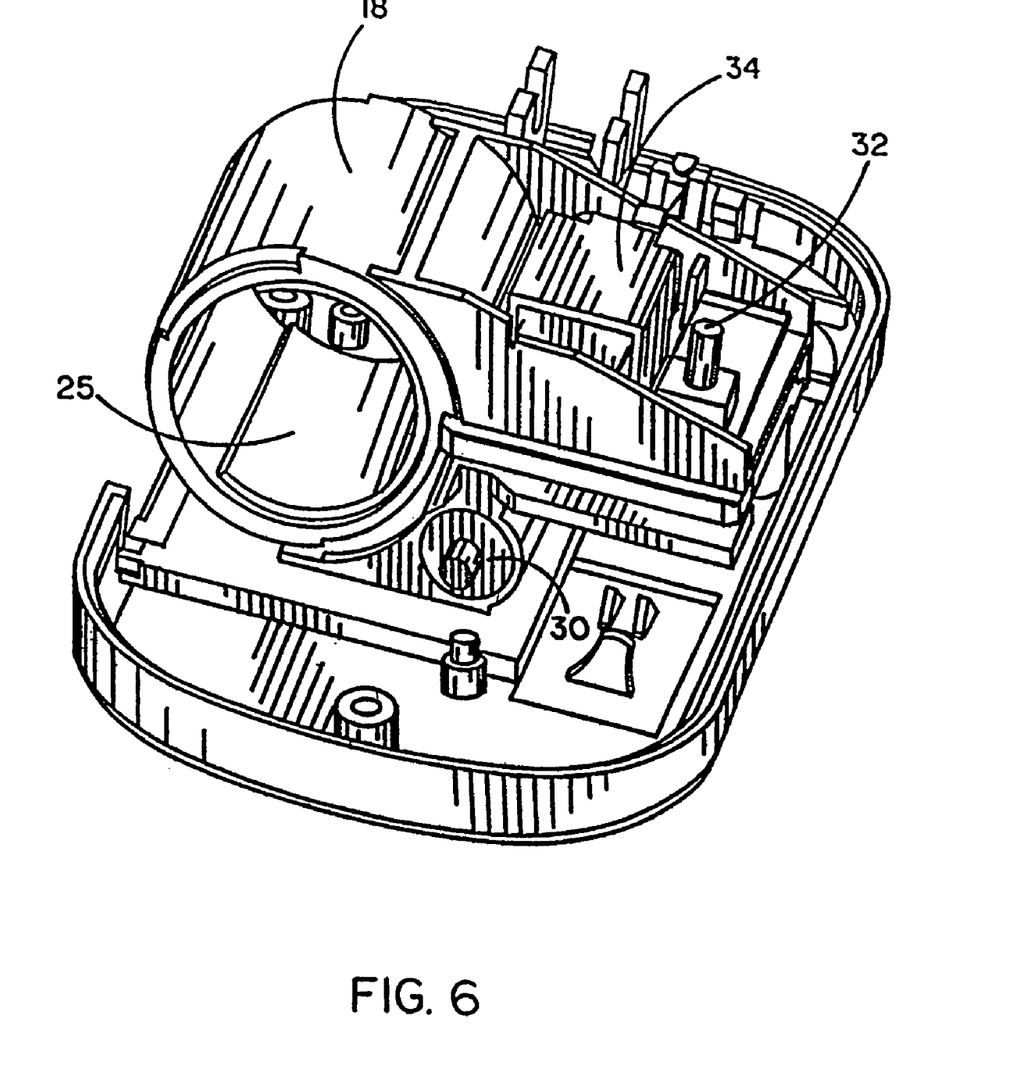
Figure 7:
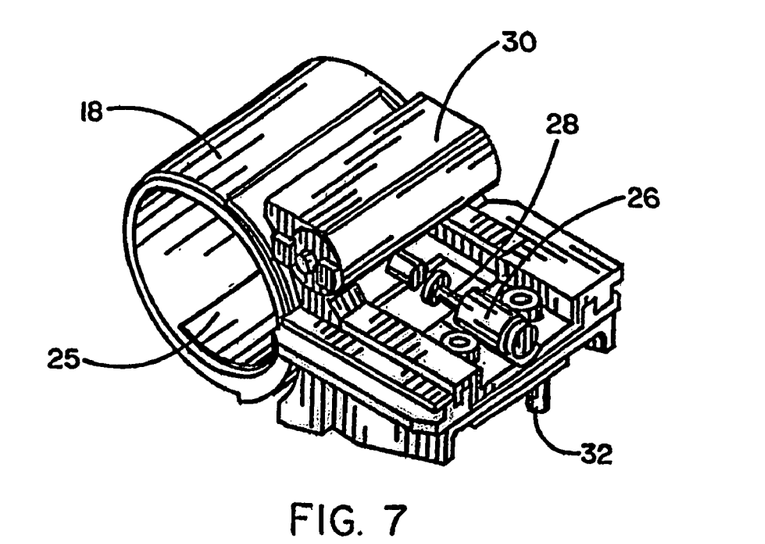
FIGS. 7 through 9 are various views of a sphygmomanometer cuff and attendant devices for applying occluding pressure to a human finger and releasing the pressure in a precise manner for carrying out the measurement.
Figure 8:
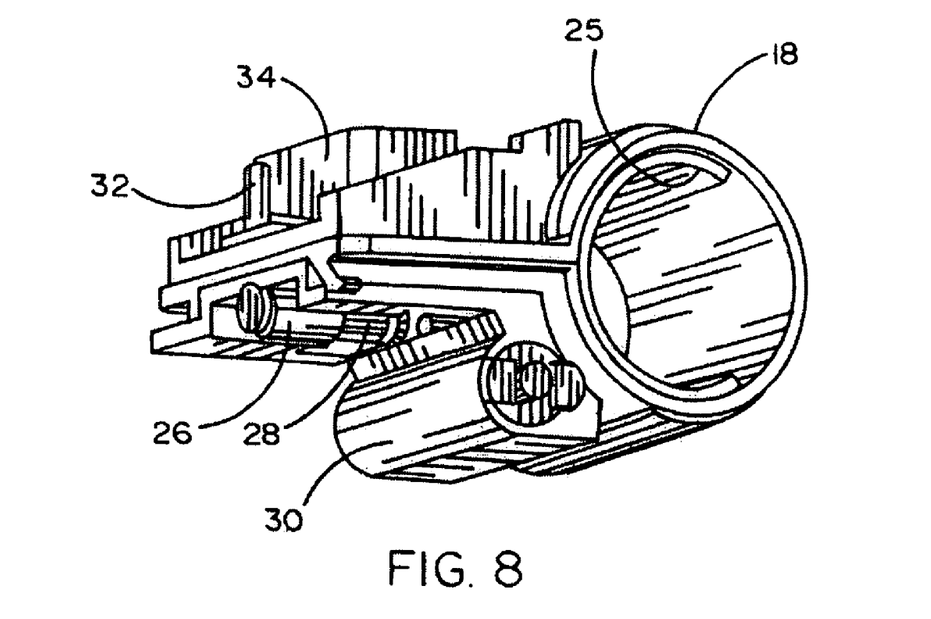
Figure 9:
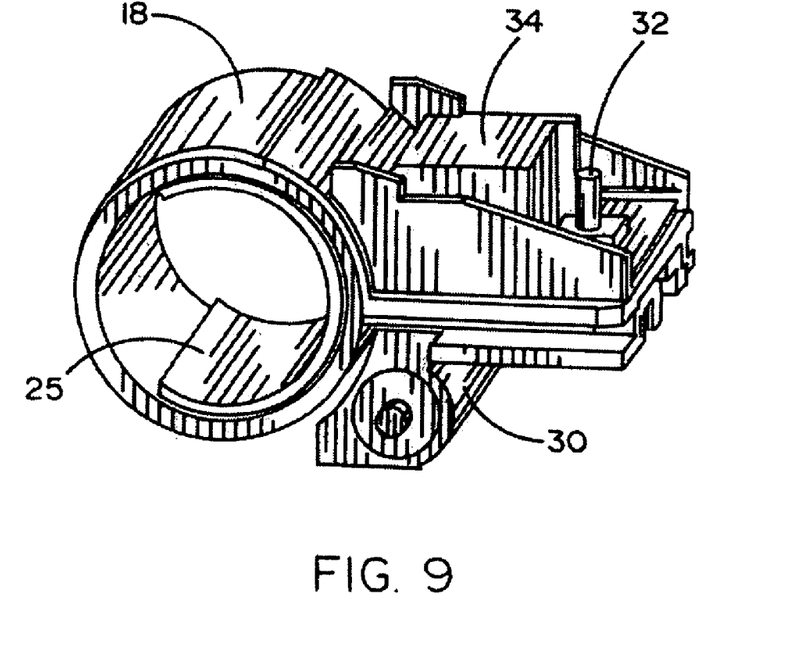

The sphygmomanometer 21 including pressure cuff assembly 18 is shown in FIG. 6 as it sits within the housing 12 and the cuff assembly and attendant components are shown in detail in FIGS. 7 to 9. As seen in those figures, the sphygmomanometer 21 comprises an inflatable air bag 25 within the annular interior of cuff assembly 18. Also forming sphygmomanometer 21 are solenoid 26, extender arm 28, motorized air pump 30, pressure sensor 32 and release valve 34. Solenoid 26 and extender arm 28 provide the ability to extend the cuff assembly 18 out of the housing 12 as previously described in conjunction with FIGS. 3 to 5. Air pump 30 provides the pressurized air to selectively expand air bag 25 to forcefully grasp a finger protruding through cuff assembly 18. Pressure sensor 32 senses the pressure at the air bag/finger surface interface and release valve 34 releases air from the air bag 25 at a rate that is commensurate with sensor 32 oscillometrically sensing the systolic and diastolic blood pressure at the inserted finger.

Figure 10:
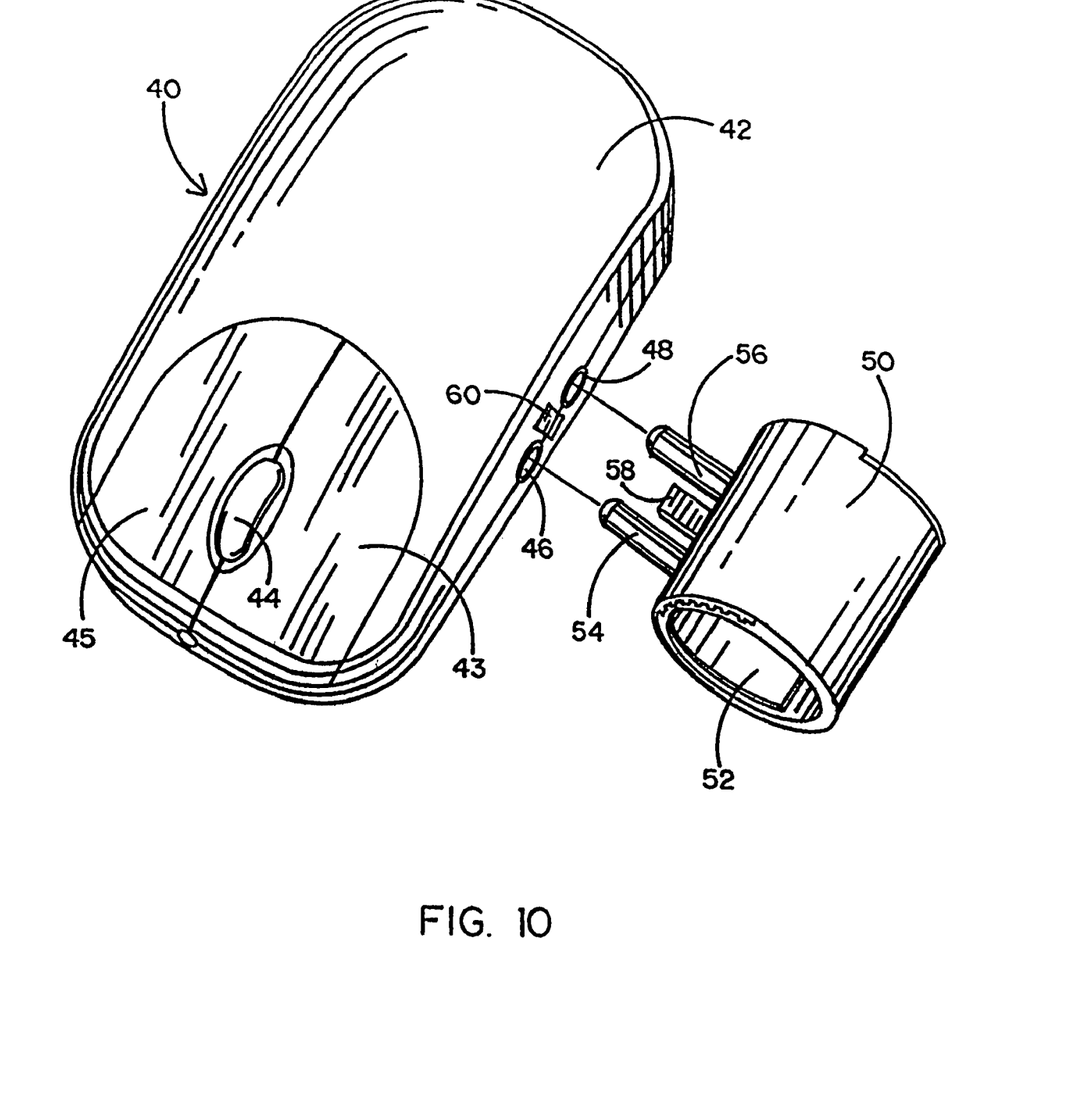
FIGS. 10 through 11 are views of a second embodiment of the invention in which a sphygmomanometer pressure cuff is selectively affixed to ports at the exterior of a mouse controller for the measurement.
Figure 11:
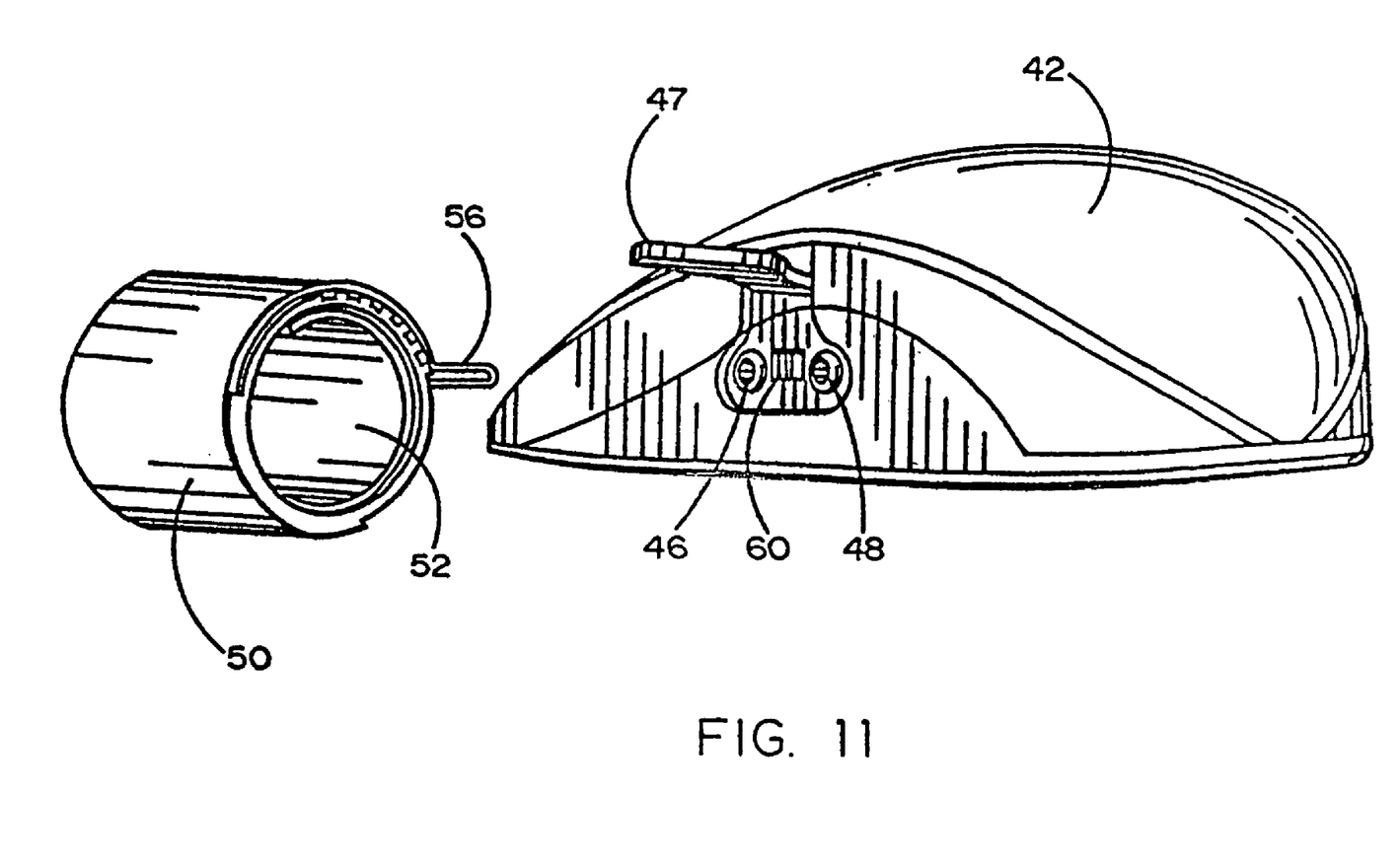

FIGS. 10 and 11 illustrate a second embodiment mouse controller 40 having a housing 42, click buttons 43 and 45 and control device 45. In this embodiment, the housing provides jacks 46 and 48 to which an external cuff assembly 50 having an air bag 52, is attached by connectors 54 and 56. A connector brace 58 mates with a brace receptacle 60 to further support the cuff assembly 50. The remaining components of the sphygmomanometer (less extender arm 28 and solenoid 26 which aren't required in this second embodiment) are interior to housing 42. Once the cuff assembly 50 is attached to the controller 40, the operation of the second embodiment is identical to that of the first embodiment 10. A jack cover 47 may be employed to protect the jacks 46 and 48 when the sphygmomanometer is not in use.

Figure 12:
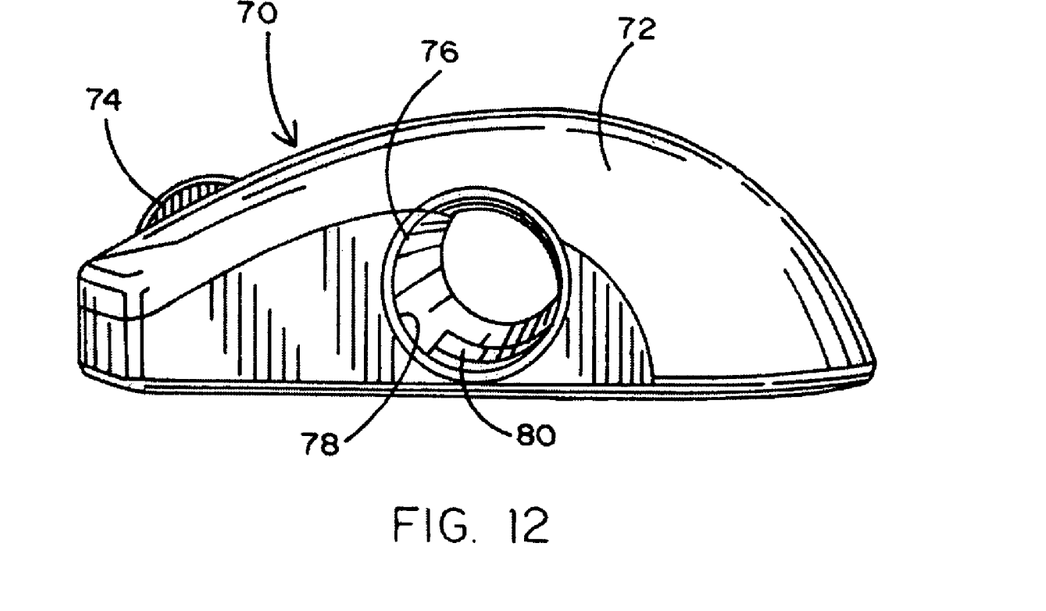
FIGS. 12 through 13 are views of a third embodiment of the invention in which a sphygmomanometer pressure cuff is fixedly positioned within the housing of a mouse controller and is accessible through at least one aperture in the housing for the measurement.
Figure 13:
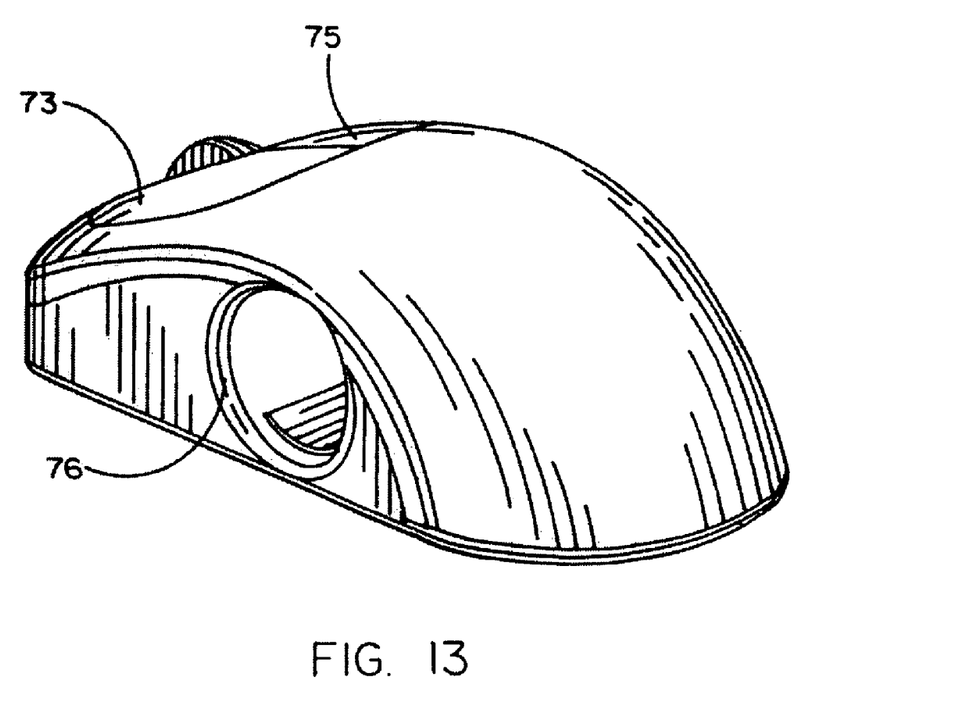

FIGS. 12 and 13 illustrate a third illustrative embodiment mouse controller 70 having a housing 72, click buttons 73 and 75 and control device 74. In this embodiment a sphygmomanometer is fully contained in a fixed position interior of housing 72 which has apertures 76 axially aligned on opposed side surfaces of the housing. Within apertures 76 is positioned a cuff assembly 78 and an air bag 80 to receive a person's finger for blood pressure and pulse rate measurement as previously described.

Figure 14:
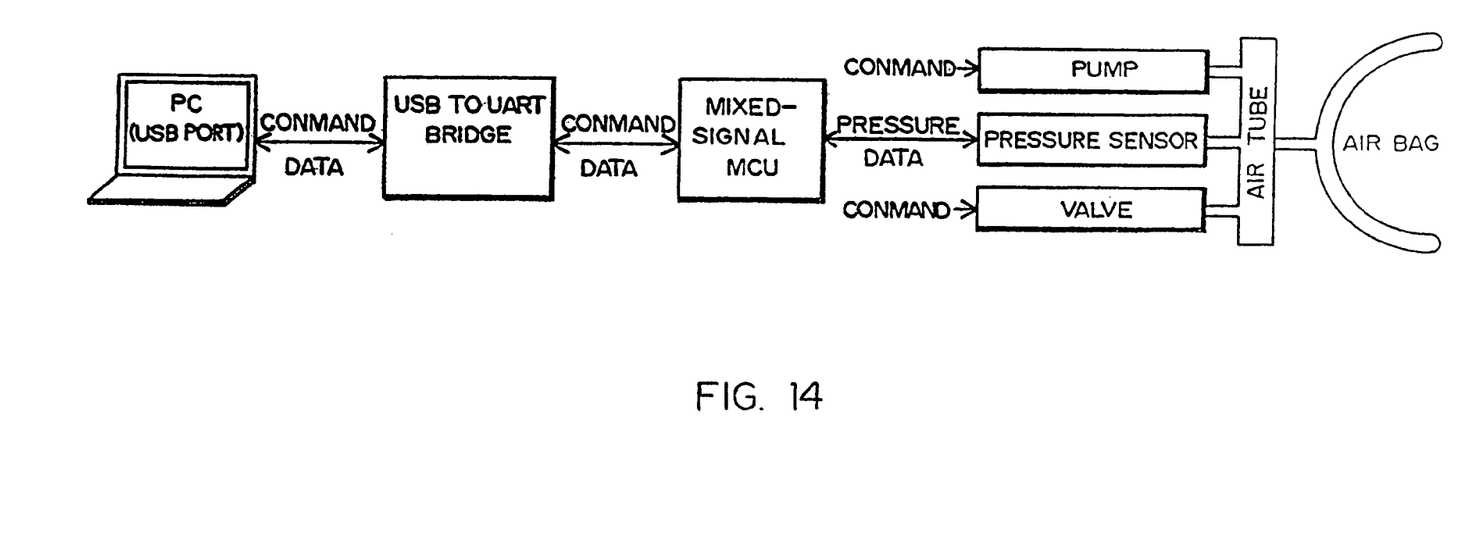
FIG. 14 is a block diagram of the sphygmomanometer and computer interface which may be employed using an embodiment of the present invention.
Figure 15:
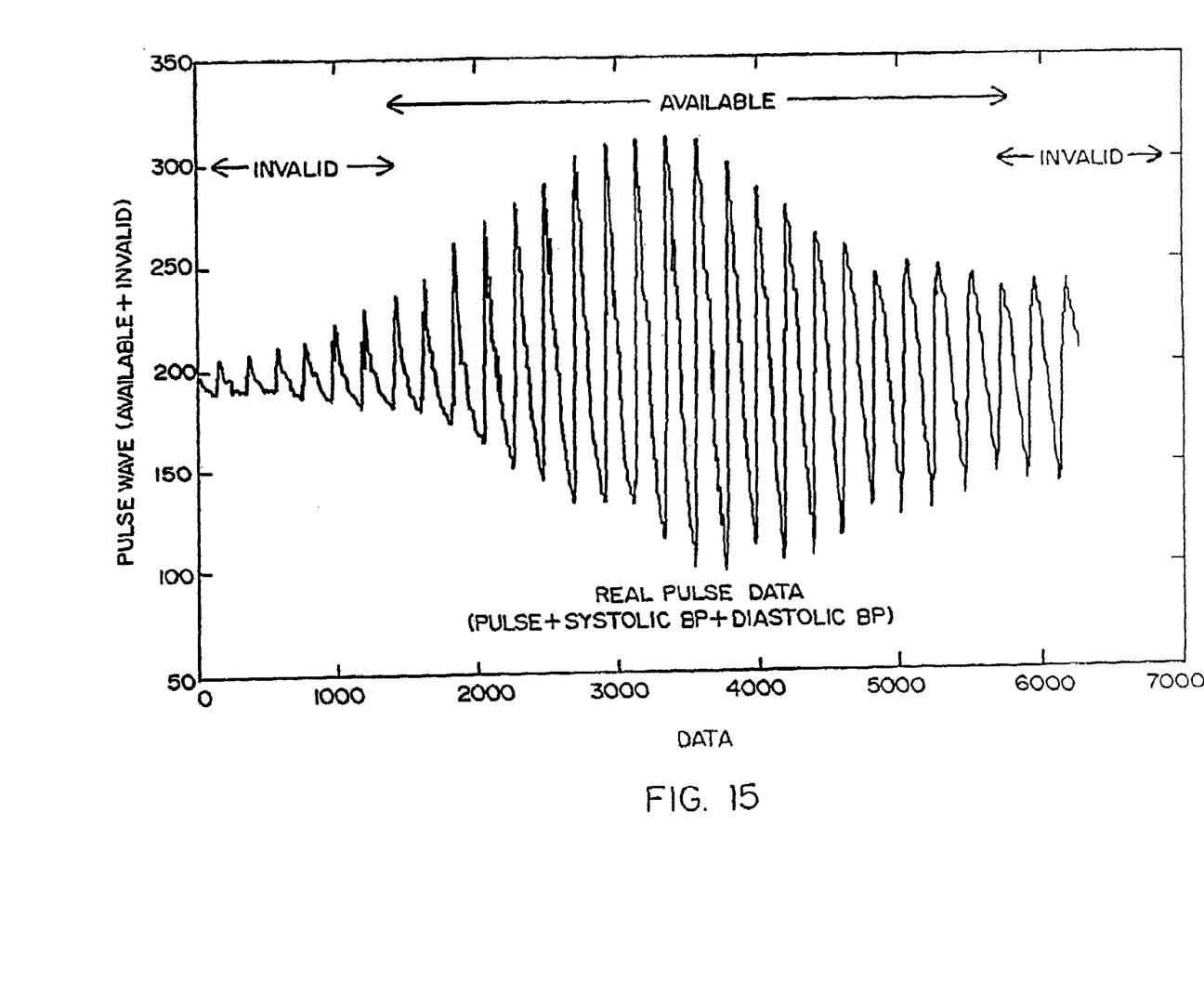
FIGS. 15 and 16 are representations of a computer monitor display of a record of blood pressure measurements.
Figure 16:
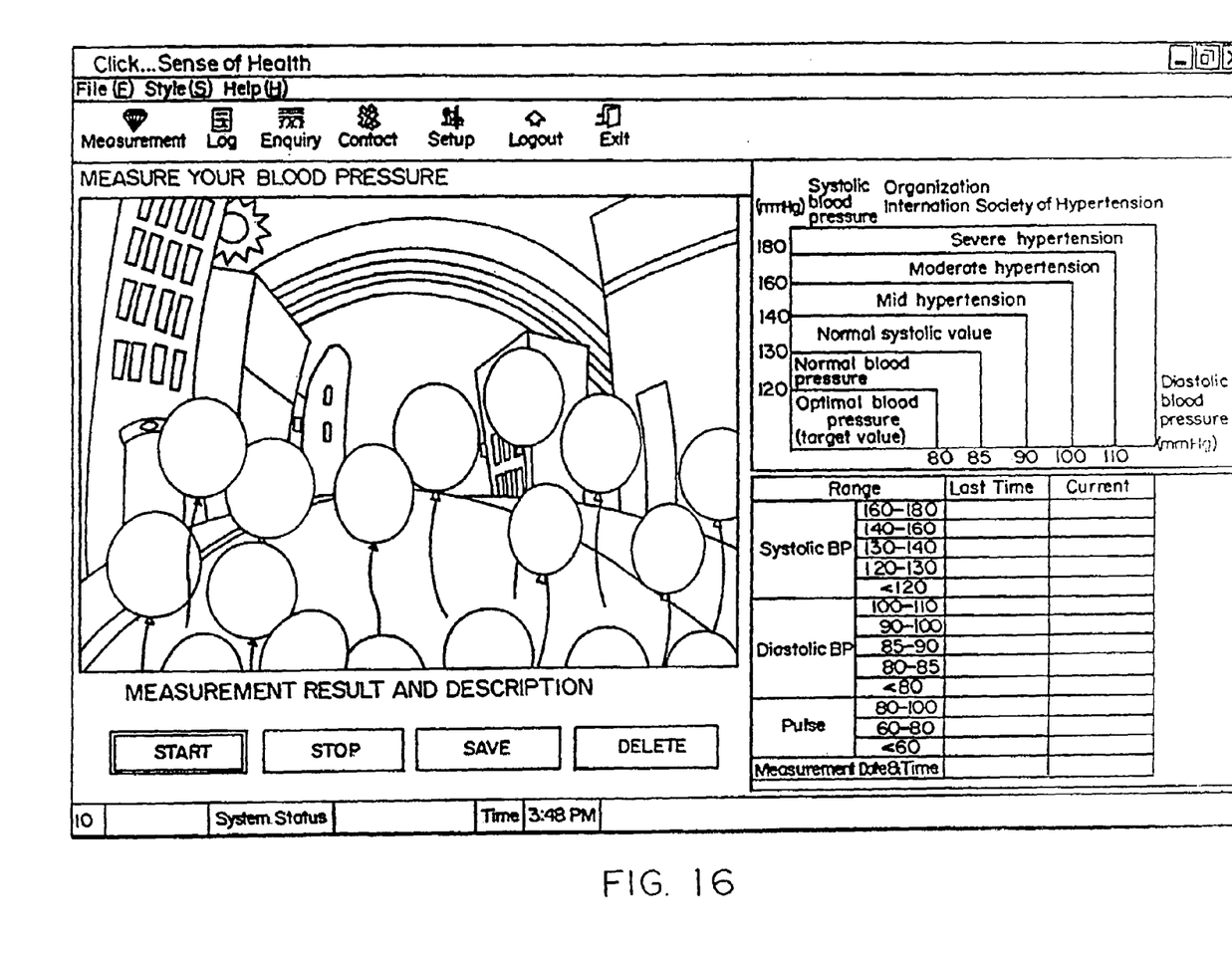
Figure 17:
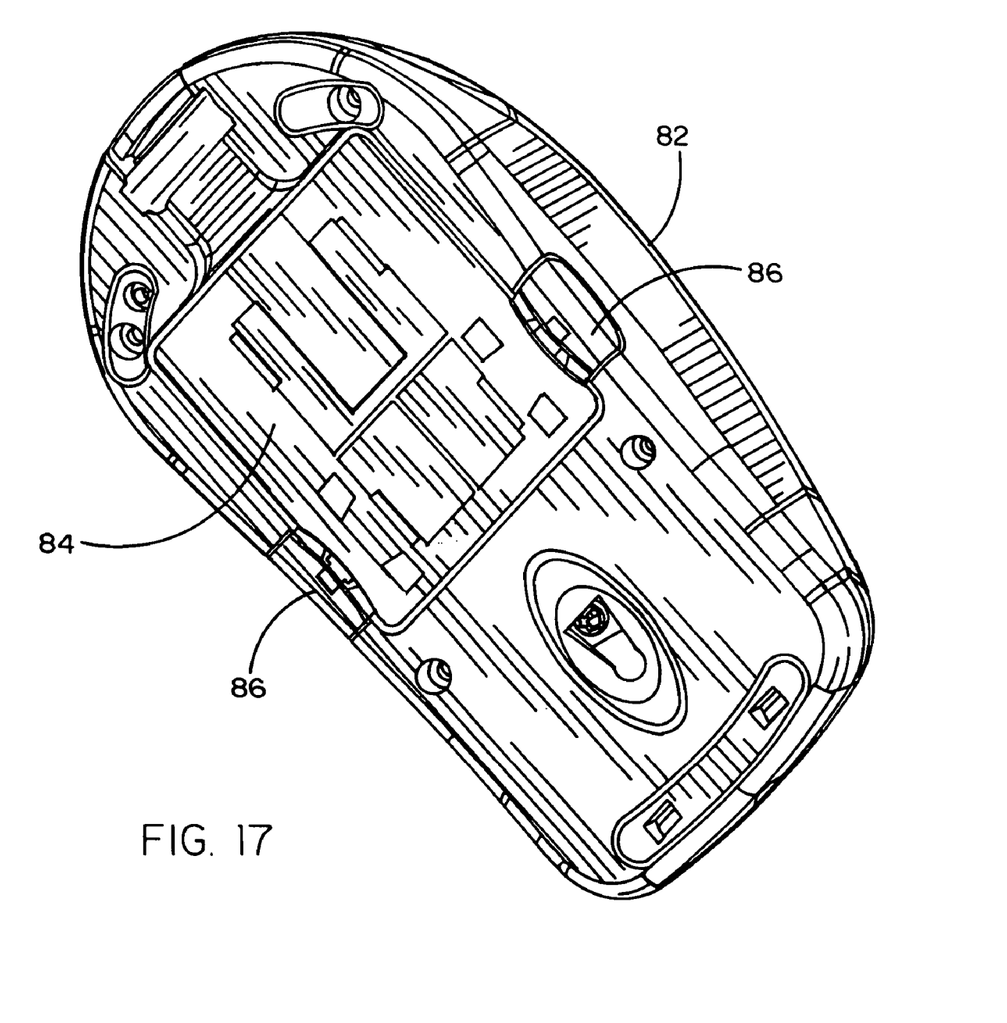
FIGS. 17 through 21 are various views of an embodiment of the invention herein where the mouse controller houses a sphygmomanometer having a wrist cuff for engaging a human wrist.
Figure 18:
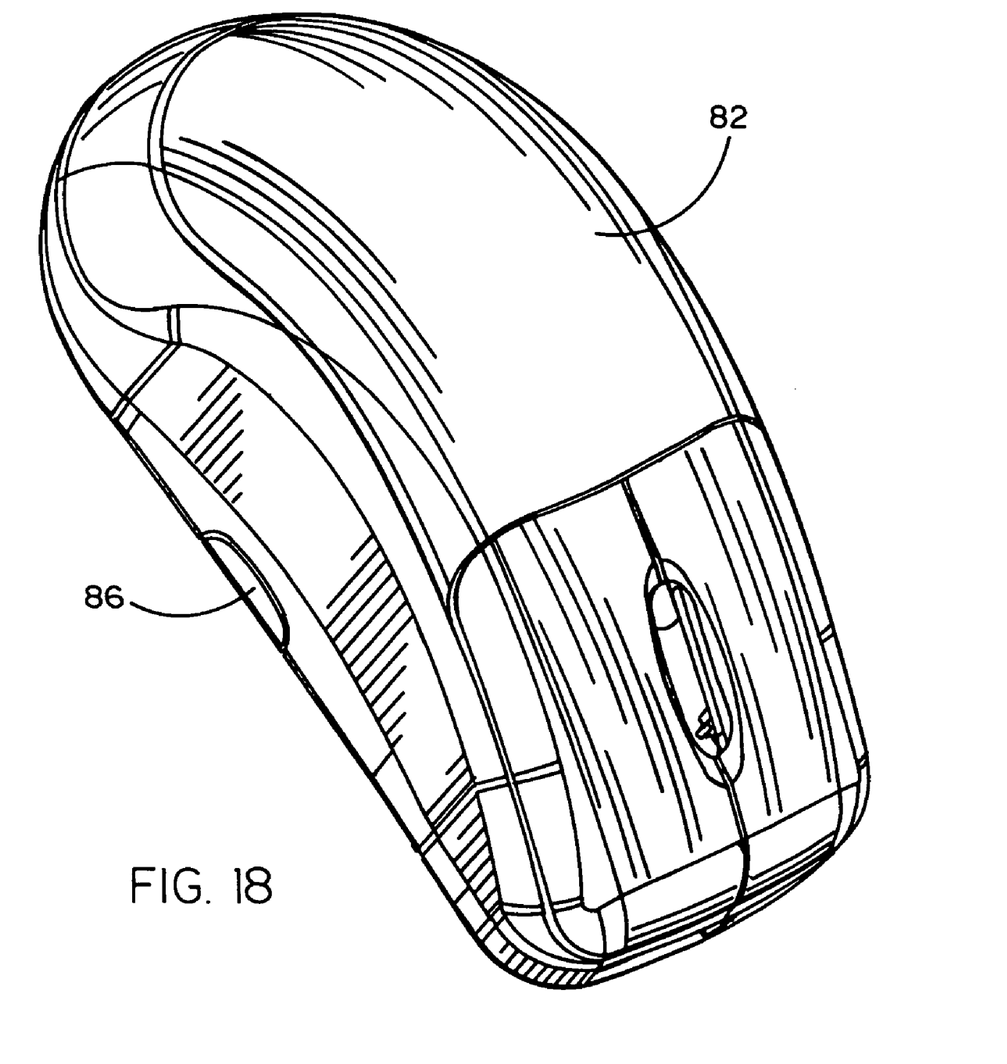

FIG. 14 is a block diagram of the sphygmomanometer/ computer interface showing that the air bag is connected through air tubes to the pump, the pressure sensor and release valve. These components, in turn, receive commands and provide pressure data to a computer through an MCU and USB to UART bridge and the computer's USB port. FIG. 15 shows the typical data transmitted to the computer during the blood pressure measurement and from which the systolic, diastolic blood pressure and pulse rate parameters are obtained. FIG. 16 illustrates a typical display presented on the computer monitor after a measurement is completed. The data may be logged and graphically displayed over multiple measurements to provide a time-based record of changes in blood pressure and pulse rate.

Figure 19:
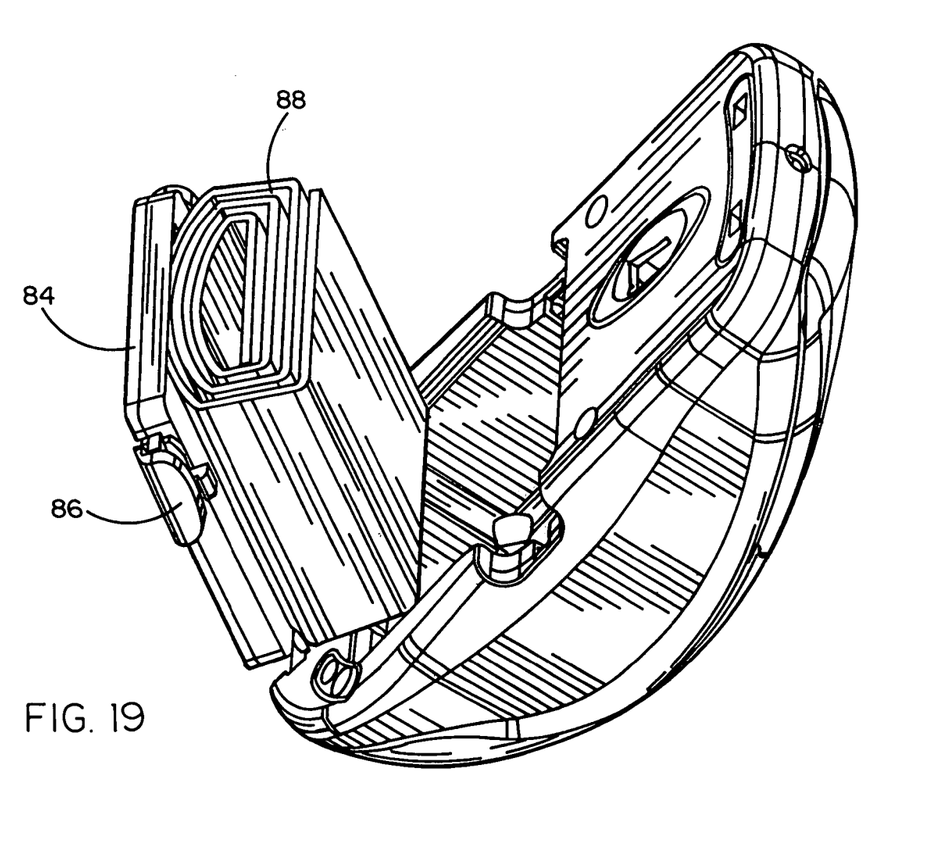
Figure 20:
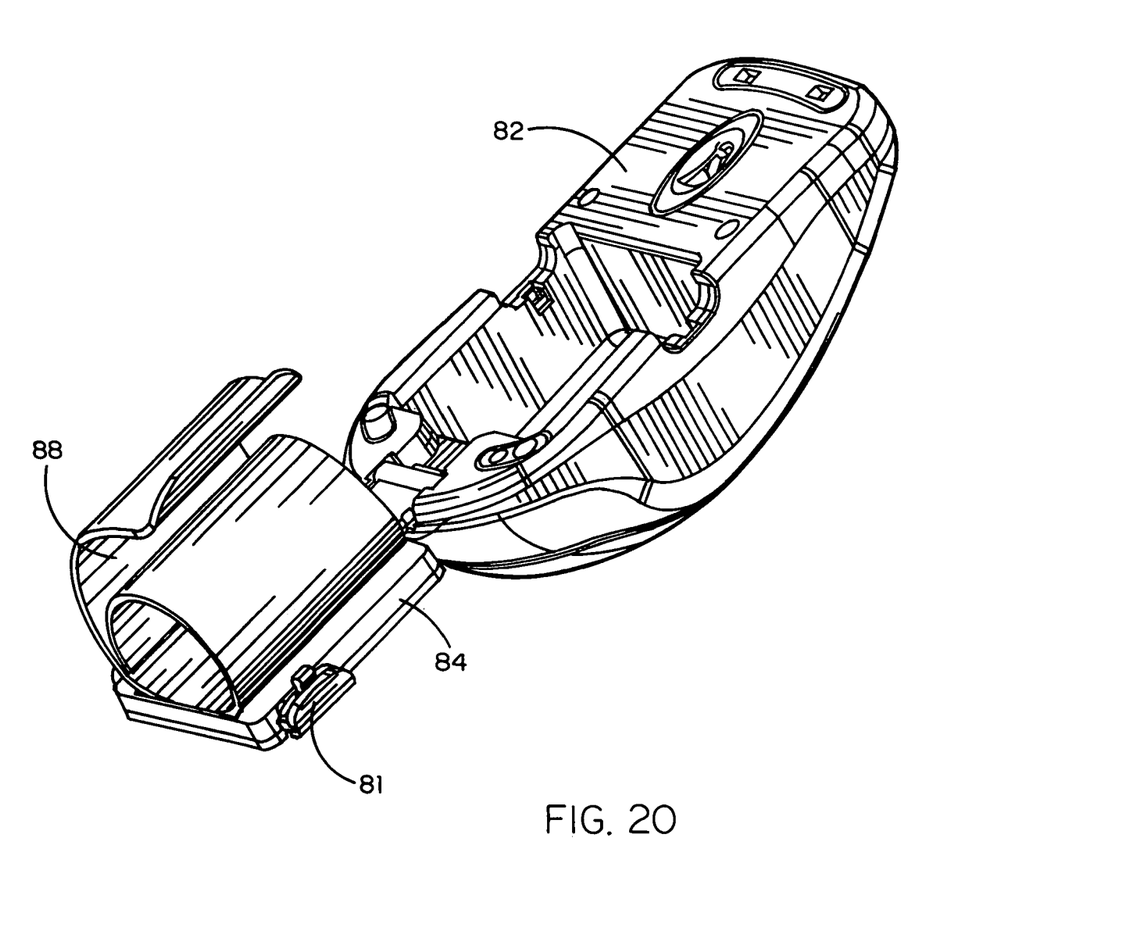
Figure 21:
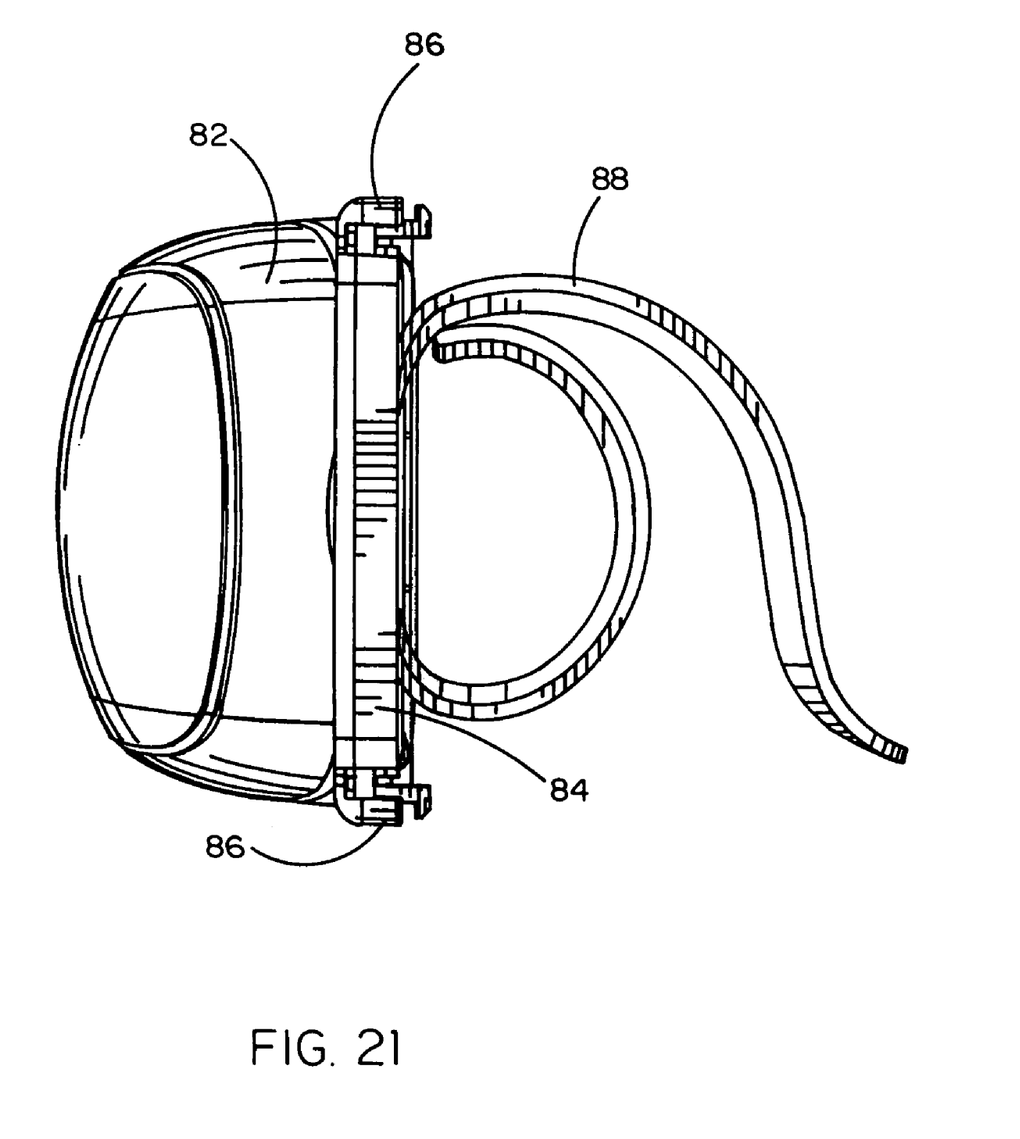

FIGS. 17 through 21 illustrate various views of still another embodiment hereof wherein a computer mouse 82 comprises a latched access door 84 along a bottom surface of the controller. The access door 84 may be released by depressing a pair of opposed latches 86 so that the door can be folded out as shown in FIG. 19 and extended to about 180 degrees relative to the bottom surface of the mouse as shown in FIGS. 20 and 21. A wrist cuff 88 is affixed to the interior of the access door 84. A user may then simply place the mouse 82 into the palm of his or her hand so that the wrist cuff 88 may be wrapped around the user's adjacent wrist. The remaining operation of the embodiment of FIGS. 17 through 21 is essentially the same as the previously described finger cuff embodiments except that the blood pressure measurement is made by the application and subsequent release of pressure via the wrist cuff 88 to the user's wrist instead of to a finger. The measurement is preferably carried out in the same way using the well-known oscillimetric technique for identifying systolic and diastolic pressure as well as pulse rate.

It will now be understood that the present invention provides a novel, convenient way of measuring and tracking health-based parameters by utilizing a modified computer mouse controller that facilitates obtaining such parameters at virtually every computer. While various alternative embodiments have been disclosed herein, other variations will now be perceived by those having the benefit of the description herein. Accordingly, the scope hereof is not limited by the illustrative features described herein, but only by the appended claims and their equivalents.

We claim:

1. A blood pressure measurement device comprising:
 a computer mouse controller having a blood pressure measuring instrument contained therein;
 an access door on said controller, said access door having at least one mechanism for opening said access door;
 said instrument having a blood pressure cuff configured for engaging a user's wrist; and
 said access door providing access to said wrist cuff upon opening of said door to permit a user to wrap said wrist cuff around the user's wrist for measuring the user's blood pressure.

2. A combined computer mouse and blood pressure measurement device comprising:
 an inflatable wrist cuff for encircling a wrist of a user to apply and release pressure for measuring diastolic and systolic blood pressure of the user;
 a computer mouse having a chamber for receiving said wrist cuff and an access door for removing said wrist cuff from said chamber; and
 a pump within said mouse and connected for air flow to said wrist cuff for inflating said wrist cuff.

* * * * *